(12) United States Patent
Markle

(10) Patent No.: US 6,702,972 B1
(45) Date of Patent: Mar. 9, 2004

(54) METHOD OF MAKING A KINK-RESISTANT CATHETER

(75) Inventor: David Reed Markle, Berwyn, PA (US)

(73) Assignee: Diametrics Medical Limited, Bucks (GB)

( * ) Notice: Subject to any disclaimer, the term of this patent is extended or adjusted under 35 U.S.C. 154(b) by 0 days.

(21) Appl. No.: 09/643,761

(22) Filed: Aug. 23, 2000

Related U.S. Application Data

(63) Continuation-in-part of application No. 09/327,420, filed on Jun. 8, 1999, now abandoned, which is a continuation of application No. 09/093,934, filed on Jun. 9, 1998, now abandoned.

(51) Int. Cl.[7] ............................ B29C 43/18; B29C 61/02
(52) U.S. Cl. ...................... 264/230; 264/130; 264/255; 264/275; 264/313; 264/334
(58) Field of Search .................. 604/526; 264/130, 264/135, 255, 275, 230, 313, 334

(56) References Cited

U.S. PATENT DOCUMENTS

| | | | |
|---|---|---|---|
| 4,650,472 A | 3/1987 | Bates | ........................ 604/158 |
| 4,737,153 A | 4/1988 | Shimamura et al. | |

(List continued on next page.)

FOREIGN PATENT DOCUMENTS

| | | |
|---|---|---|
| EP | 0 617 977 A1 | 2/1994 |
| WO | 97/37713 | 10/1997 |
| WO | 97/48437 | 12/1997 |

OTHER PUBLICATIONS

Definition of "cathether" from Webster's Ninth New Collegiate Dictionary, 1990, p. 216.*

Primary Examiner—Edmund H. Lee
(74) Attorney, Agent, or Firm—Merchant & Gould, P.C.

(57) ABSTRACT

A catheter which has resistance to collapsing when bent, and a method for producing such a catheter. The method includes (i) supporting a helical metallic coil having turns on a mandrel which has a release surface comprising a polytetrafluoroethylene (PTFE) or fluorinated ethylene propylene copolymer (FEP) tube supported on the mandrel; (ii) introducing the helical coil while supported on the mandrel into a first tube, the first tube being formed from a material which is flowable at a first elevated temperature and said first tube being received within a second tube, the second tube being heat shrinkable at a second temperature which is equal to or greater than the first temperature; (iii) heating the resulting assembly to a temperature equal to or greater than the second temperature, whereby shrinkage of the second tube causes material of the first tube to flow between turns of the coil and substantially encapsulate the coil; (iv) removing the mandrel while leaving the sheathing tube within the coil; and (v) removing the sheathing tube by tensioning the tube longitudinally of the coil. Catheters having small internal bores and very thin walls are prepared by this method. The catheter includes a first, thermo-flowed tube having a helical coil at least partially enveloped in the material of the tube. A second tube surrounds the first tube and is formed from heat shrunk material.

6 Claims, 5 Drawing Sheets

U.S. PATENT DOCUMENTS

| | | | |
|---|---|---|---|
| 4,889,407 A | 12/1989 | Markle et al. | 350/96.29 |
| 4,955,862 A | 9/1990 | Sepetka | |
| 5,069,674 A * | 12/1991 | Fearnot et al. | 604/282 |
| 5,180,376 A | 1/1993 | Fischell | |
| 5,262,037 A | 11/1993 | Markle et al. | 204/415 |
| 5,279,596 A | 1/1994 | Castaneda et al. | |
| 5,290,266 A | 3/1994 | Rohling et al. | |
| 5,305,740 A * | 4/1994 | Kolobow | 128/207.14 |
| 5,380,304 A | 1/1995 | Parker | 604/282 |
| 5,658,264 A * | 8/1997 | Samson | 604/282 |
| 5,669,920 A | 9/1997 | Conley et al. | |
| 5,676,784 A | 10/1997 | McGaffigan | |
| 5,700,253 A | 12/1997 | Parker | 604/282 |
| 5,702,373 A | 12/1997 | Samson | |
| 5,755,704 A * | 5/1998 | Lunn | 604/282 |
| 5,797,876 A | 8/1998 | Spears et al. | |
| 5,827,242 A * | 10/1998 | Follmer et al. | 604/282 |
| 5,891,114 A | 4/1999 | Chien et al. | |
| 5,947,940 A | 9/1999 | Beisel | |
| 5,951,929 A | 9/1999 | Wilson | |
| 5,954,651 A | 9/1999 | Berg et al. | |
| 6,019,736 A | 2/2000 | Avellanet et al. | |
| 6,187,130 B1 * | 2/2001 | Berard et al. | 156/294 |

\* cited by examiner

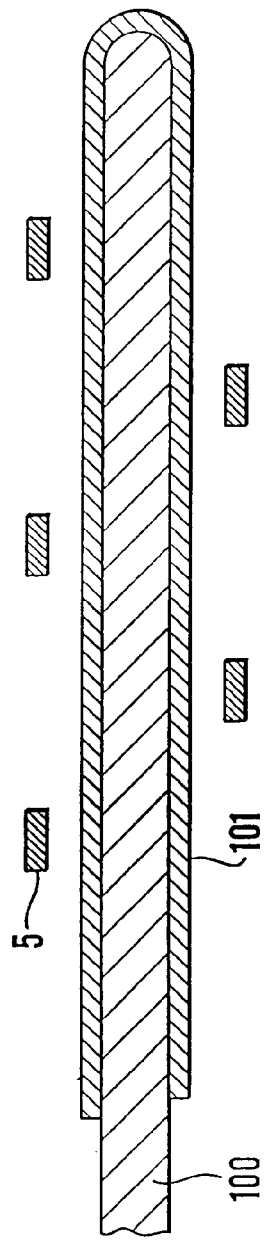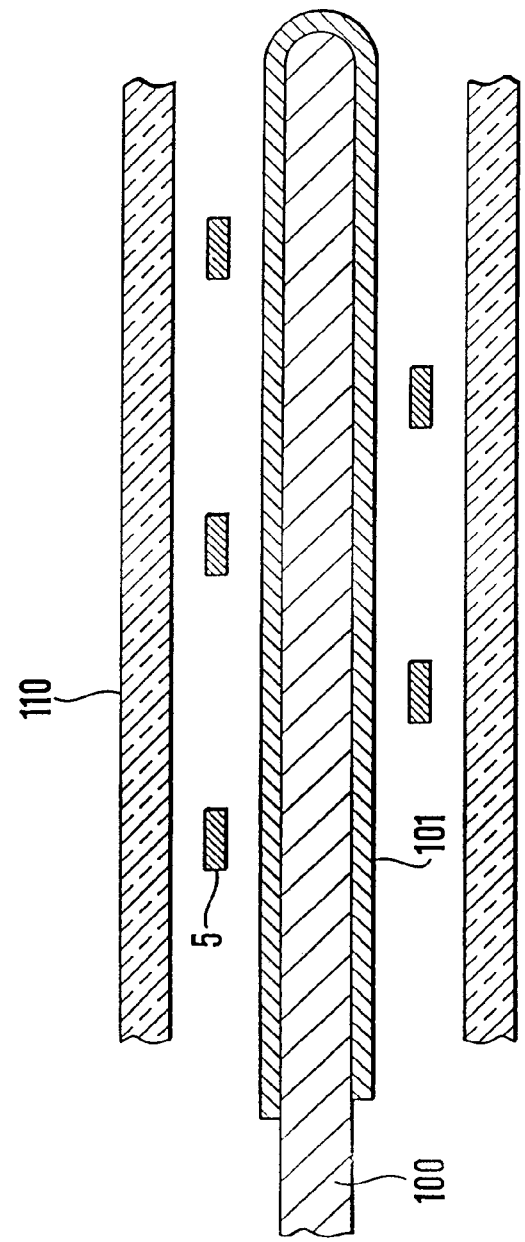
Fig.2
Fig.3

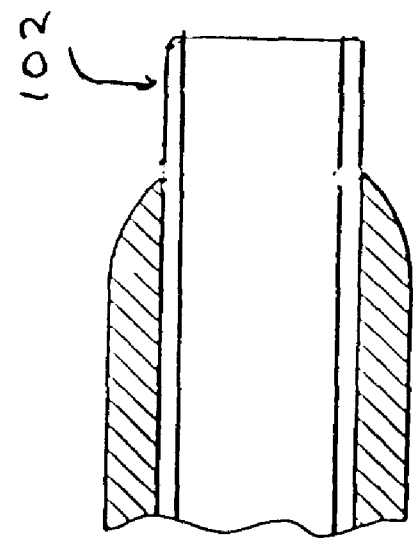
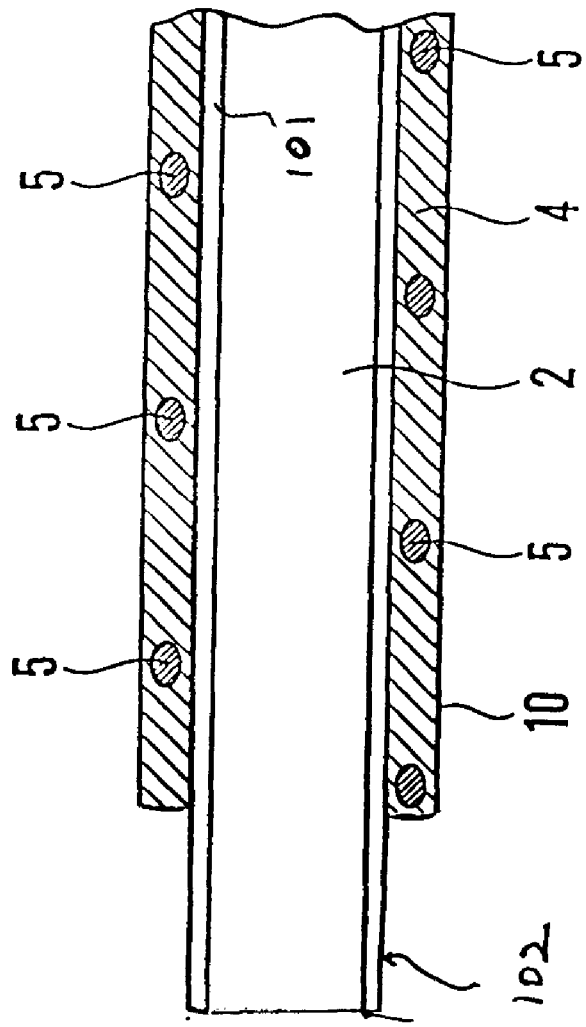
Fig. 5a

METHOD OF MAKING A KINK-RESISTANT CATHETER

CROSS REFERENCE TO RELATED APPLICATION

This application is a continuation-in-part of application Ser. No. 09/327,420, filed Jun. 8, 1999, now abandoned, which is a continuation in part of application Ser. No. 09/093,934, filed Jun. 9, 1998, now abandoned, for a Catheter.

TECHNICAL FIELD

This invention relates to catheters especially, but not exclusively, for intravascular sensors such as those which measure $pO_2$, $pCO_2$, pH and temperature.

BACKGROUND OF THE INVENTION

Catheters are often used to introduce sensing elements into the body, particularly into a blood vessel. Usually a hollow needle is used for making an initial entry into the blood vessel. A wire guide is then passed into the needle and the needle is then withdrawn. A catheter can then be slid over the wire guide and introduced into the blood vessel. After removing the wire guide, a sensor, e.g. including one or more optical fibres are then passed into the catheter. Often such catheters have a small diameter and thin walls and kink easily. Should the catheter kink, the sensor may give a false reading or be damaged. Replacement of a damaged sensor is relatively expensive and while a change is made to a new sensor, monitoring of a patient's condition is interrupted.

Various attempts have been made to render catheters or introducer sheaths resistant to kinking. One procedure is described in European patent application No. 0617977 which describes an introducer in which a helical coil is sandwiched between an inner tube of PTFE and an outer tube of heat formable polyamide resin. The outer tube is heat formed and compressed so that material passes between turns in the coil and forms a connection with the roughened outer surface of the inner tube. It is difficult to control the manufacture to cause material from the outer tube to flow between the turns of the coil without distorting the inner tube. Also the reinforced introducers described in the above reference are relatively thick because they consist of two tubes with a coil sandwiched between them.

SUMMARY OF THE INVENTION

One object of the invention is to provide a more reliable and simpler method of producing a kink-resistant catheter.

Another object is to produce a kink-resistant catheter consisting of a tube having a thin wall in which a reinforcing coil is embedded and a method of its production.

A related object is to provide a reinforced catheter suitable for introducing or guiding a sensor into human tissue, such as a blood vessel, while resisting kinking and protecting the sensor from damage should the catheter be disturbed.

Another object is to provide a simple and reliable method of providing a tapered end to the catheter.

Such sensors are typically constructed with sensing elements each of about 0.002 inches diameter, in the case of wire and 0.007 inches in diameter in the case of optical fibres. When sensing elements for all four parameters are present, the sensor has an overall diameter of approximately 0.02 inch (0.5 mm). This small size is necessary to allow the sensor to be placed in an artery through a cannula and not compromise the primary function of the cannula of monitoring blood pressure and allowing blood samples to be taken.

The small size of the sensors means that they are fragile. Bending of optical fibre sensors results in a change in the signals. Progress has been made in reducing the impact of this by providing a second, reference wavelength but until the advent of this invention, sensor kinking remained a problem.

According to one aspect of the invention there is provided a method of making a kink-resistant catheter, said method comprising the steps of:

(i) supporting a helical coil having a plurality of turns on a mandrel which extends though the coil and is covered with a release surface;

(ii) introducing the helical coil while supported on the mandrel into a first tube, said tube being formed from a material which is flowable at a first elevated temperature and said first tube being received within a second tube, said second tube being heat shrinkable at a second temperature which is equal to or greater than said first temperature;

(iii) heating the resulting assembly to a temperature equal to or greater than said second temperature, whereby shrinkage of the second tube causes material of said first tube to flow between turns of the coil and substantially encapsulate the coil; and (iv) removing the mandrel, the release surface and the second tube.

In some embodiments of the invention the first tube comprises polyethylene or polyurethane and the second tube comprises polyester, PTFE or FEP. FEP can be the second, heat-shrinkable tube in cases where the first tube is flowable at temperatures at which FEP does not flow but is heat-shrinkable. The most preferred combination is to employ a first tube which is polyurethane and a second tube which is FEP. Materials which are chemically very similar, e.g. PTFE and FEP, should not be used in conjunction as the first and second tubes because they tend to bond together.

Preferably the first tube is heat flowable at a first temperature in the range 100 to 300° C. (212 to 572° F.) and the second tube is heat shrinkable at a second temperature equal to or greater than the first temperature and preferably in the range 150 to 350° C. (302 to 662° F.).

In the manufacture of the reinforced catheter, the helical coil can be mounted on a mandrel and then introduced into the first tube, which is received within the second tube. A release surface is provided on the mandrel to facilitate removal of the mandrel after formation of the reinforced catheter. Suitable release agents include liquid release agents such as silicone oils. However, it is preferred, for two reasons, to use a solid release coating such as a PTFE or FEP tube, fitted onto the mandrel. First, it is found that when the mandrel carries a PTFE or FEP tube, the assembly does not adhere to the mandrel in the heating step and the mandrel can be easily drawn out from the assembly. Also, by using a PTFE or FEP sheathing tube on the mandrel, the flowable plastic of the first tube is effectively squeezed between the second tube and the inner release tube during the heating step. This enables higher temperatures to be employed which ensures that the plastic of the first tube flows to encapsulate the helical coil. At the same time, a second tube and the PTFE or FEP mandrel sheathing tube ensure that a smooth surface is formed on the inner and outer surfaces of the thus formed reinforced catheter. While a mandrel comprising a polished metal surface is satisfactory when used with a release agent such as a silicone oil, the presence of small scratches can cause adhesion and difficulty in removing the mandrel from the assembly.

However, the provision of a PTFE or FEP sheath tube on the mandrel can give rise to another difficulty in practice. This arises because, after removal of the mandrel, the sheathing tube is found to have adhered to the inside of the assembly. The Applicants have found that a reliable way of removing the sheathing tube in these circumstances is to apply a longitudinal tensioning force to the sheathing tube. This is best done by making the PTFE sheathing tube longer than the assembly of first and second tubes and helical coil so that the sheathing tube extends beyond one or, preferably both, ends of the assembly. Thus, after the heating step, the sheathing tube can be tensioned, preferably by pulling it outwardly at both ends. This action reliably breaks the adhesion with the inside of the assembly so that the sheathing tube can be removed.

Preferably, the second tube is also removed after the heating step. This is conveniently accomplished by slitting the tube lengthwise.

In this way, a catheter of small diameter and very thin wall thickness is obtained, which nevertheless is highly resistant to kinking.

In some embodiments of the invention the tubes extend beyond one or both ends of the helical coil.

The invention also encompasses a method of making a kink-resistant catheter which method comprises forming an assembly by the steps of:

(i) supporting a helical metallic coil having a plurality of turns on a mandrel which has a release surface comprising a polytetrafluoroethylene (PTFE) or fluorinated ethylene propylene copolymer (FEP) sheathing tube supported on the mandrel;

(ii) introducing the helical coil while supported on the mandrel into a first tube, said first tube being formed from a material which is flowable at a first elevated temperature and said first tube being received within a second tube, said second tube being heat shrinkable at a second temperature which is equal to or greater than said first temperature;

(iii) heating the resulting assembly to a temperature equal to or greater than said second temperature, whereby shrinkage of the second tube causes material of said first tube to flow between turns of the coil and substantially encapsulate the coil;

(iv) removing the mandrel while leaving the sheathing tube within the coil; and (v) removing the sheathing tube by tensioning said tube longitudinally of the coil.

According to the invention there is further provided a catheter which comprises a helical metallic coil having a plurality of longitudinally spaced apart turns, said coil being substantially encapsulated in a matrix comprising a tubular member of heat-flowable material which extends between turns of the coil, said tubular member having an exposed outer surface and an inner surface covering said spaced apart turns, and wherein the coil terminates inwardly of at least one end of the tubular member and wherein an inwardly tapered tip is present at said end.

The helical coil is metallic, for example, stainless steel and preferably the coils have a rounded cross-section, e.g. a circular cross-section. In some embodiments of the invention, a non-magnetic helical coil is used. An example is the metallic alloy known as MP35-N. Non-magnetic coils can be advantageous since adverse interactions with nuclear magnetic resonance systems, for example for imaging, can be reduced or eliminated.

The first tubular member may comprise polyethylene or polyurethane. The second tubular member may comprise PTFE, polyester or FEP.

Preferably the catheter has a tapered tip, the helical coil terminating inwardly of the tip. Provision of a tapered tip greatly improves the case of introducing the catheter into a blood vessel.

Advantageously, a reinforced catheter of very small wall thickness can be made by removing the second tube after the first tube has been caused to flow through turns in the helical coil. This can be readily achieved, for example, by providing a second tube which extends beyond an end of the first tube, forming a slit in the projecting end of the second tube after the heat shrinkage step and peeling the second tube away from the first. By selecting materials for the first and second tubes as described above, the first tube does not bond to the second and can easily be parted. The preferred procedure is to first remove the mandrel. Sometimes the sheathing tube comes away with the mandrel. More commonly, however, the mandrel is removed leaving the sheathing tube within the encapsulated helical coil. As mentioned above, the sheathing tube can be removed in these circumstances by applying a tension to opposite projecting ends of the sheathing tube.

After the sheathing tube has been removed, the inside diameter of the reinforced catheter is slightly larger so that a metal rod or wire support of correspondingly larger diameter is inserted into the bore of the catheter. The second tube is then removed, preferably by the technique described above, while supporting the assembly on the metal rod or wire support.

The reinforced catheters of the invention have the same or similar inside and outside diameters as conventional un-reinforced catheters but are extremely flexible and resistant to flattening when bent around a tight curve.

BRIEF DESCRIPTION OF THE DRAWINGS

Embodiments of the invention will be described by way of a non-limiting example by reference to the accompanying figures of which:

FIG. 1a is a scrap longitudinal view of the tip of a modified catheter of the invention;

FIG. 2 is a scrap section of a spring and a mandrel which carries a sheathing tube forming a release layer;

FIG. 3 is a scrap section of a spring and a sheathing tube carried on the mandrel, the mandrel being received within a first tube;

FIG. 5a is a scrap section of the embodiment shown in FIG. 5 but before removal of the sheathing tube.

Figure 1:
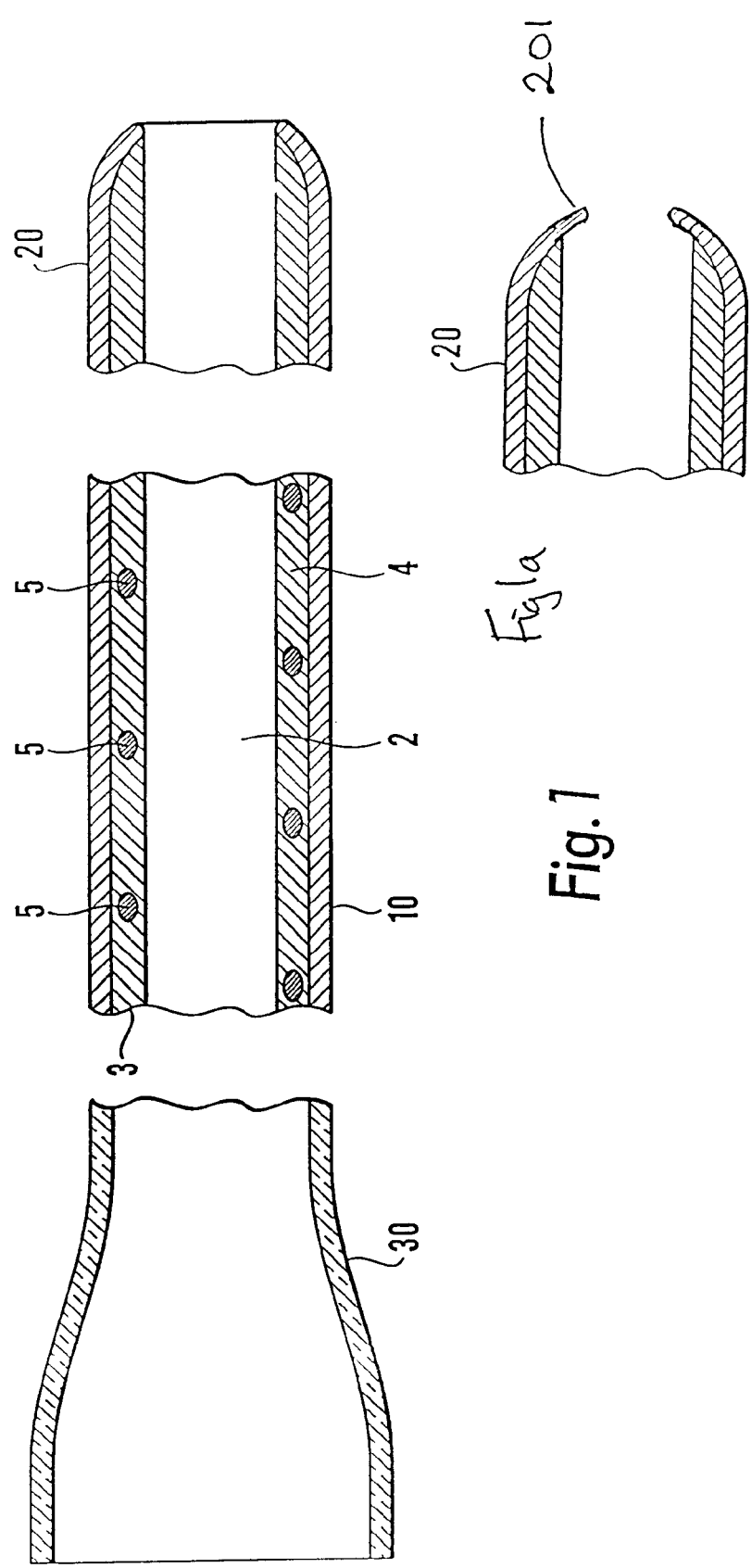
FIG. 1 is a scrap longitudinal section of a catheter of the invention.
Figure 4:
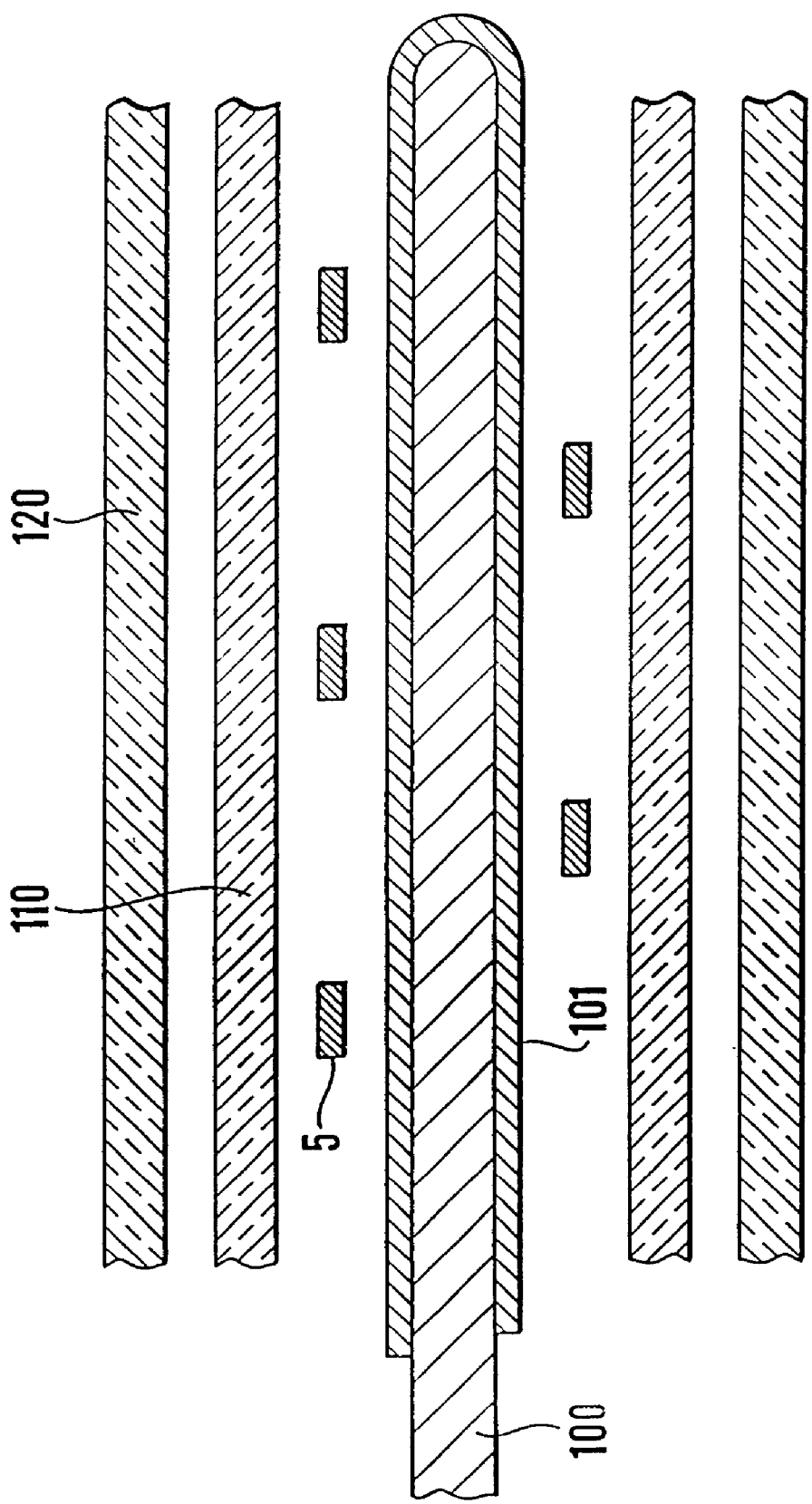
FIG. 4 is a scrap section of a mandrel carrying and received within concentric first and second tubes.

A catheter 1 of the invention is shown in section in FIG. 1. It is generally cylindrical and flexible and has an axial bore 2. Axial bore 2 is defined in the illustrated embodiment by first tubular member 3. Tubular member 3 is of composite structure. It comprises a matrix 4 of heat-flowed plastics material such as polyethylene or polyurethane. A helical coil 5 is present within matrix 4 and is substantially completely encapsulated in the matrix. Helical coil 5 provides hoop strength to the catheter and hence kink resistance. Helical coil 5 is preferably metallic such as stainless steel for example a grade available as 304 VSS-D.D (diamond drawn). Preferably the helix wire is of circular cross section although other cross sections can be used, such as rectangular, as shown in FIGS. 2 to 4. The turns of the helical coil 5 are conveniently spaced apart. For example in one embodiment of the invention a cylindrical helix wire about 0.05 mm (0.002") diameter can have a pitch of about 0.01 mm (0.004").

The first tubular member is received in a second tubular member 10. The second tubular member 10 is essentially non-adherent to the first tubular member. This condition may be obtained by selecting materials which are chemically somewhat dissimilar. Second tubular member 10 comprises heat-shrunk material such as heat shrink PTFE (polytetrafluoroethylene), polyester or FEP.

It is preferred that the tip 20 of the catheter tapers inwardly. Helical coil 5 may not extend to the tip 20 and preferably does not do so. A reason for this will be explained hereinafter.

A hub 30 such as a luer hub can be fitted to the end of the catheter opposite to the tip 20. A needle (not shown) can be fitted to the tip of the catheter.

The flexibility of the catheter can be varied by, for example, varying the stiffness of the helical coil. Those skilled in the art will have little difficulty in varying the flexibility of the helical coil, for example, by varying the material of which it is made or the thickness of the wire. The flexibility of the catheter can be varied in other ways such as varying the thickness or the nature of the heat flowed plastics material forming the first tube.

A convenient way of the manufacturing the catheter will now be described by reference to FIGS. 2, 3, and 4. Mandrel 100 is conveniently a rigid metallic material, e.g. a stainless steel wire. A release layer 101 in the form of a thin PTFE or FEP tube is present on the mandrel 100. A PTFE or FEP tube is advantageous because of its chemical inertness. The release layer tube is snugly fitted onto the mandrel. A helical coil 5 as described previously is slid onto the mandrel 100 over the release layer tube 101. The internal diameter of the helical coil 5 is preferably slightly larger than the external diameter of the mandrel 100. In an example the mandrel was about 0.05 mm (0.002") less in diameter than the internal diameter of the coil 5. A tube of plastics material 110 flowable at a first, elevated, temperature is slid over the helical coil. In many cases the heat flowable material 110 is the same as the heat flowed plastics of matrix 4. It is not essential however since material 110 could be a material which undergoes a chemical or physical transformation on heating so that it is not heat flowable on a further heating. Suitable materials include polyethylene and polyurethane.

A second tube 120 of heat shrinkable plastics material is then slid over the first tube to make an assembly. PTFE, polyester or FEP are preferred materials. The second tube is heat shrinkable at a temperature greater than a temperature at which the first tube is flowable, and does not flow at the temperature at which the first tube begins to flow. It will be appreciated that the coil is a relatively snug fit over tube 101 on the mandrel and similarly, the first tube fits relatively closely to the helical coil, while the second tube also fits closely to the first tube. For better clarity, the distances between the various components are exaggerated in FIGS. 2 to 4.

In a preferred embodiment of the invention the helical coil does not extend to the tip of the tubes. Where the coil does not extend to the tip of the tubes a tapered portion is formed. This taper, which may be trimmed during a finishing step, facilitates introduction of the catheter into the body.

The assembly of mandrel coil, first and second tubes is then heated, e.g. in an oven or by means of a radiant heating element or elements directing heat onto the outer surface of the second tube 120. In one embodiment, the radiant heater is annular and the assembly in advanced at an appropriate speed through the annulus of the heater. The duration of heating is sufficient to ensure that the entire assembly is heated to the same temperature, such temperature being high enough to cause the material of the first tube to flow and the material of the second to shrink. The mandrel may be removed, preferably after the heating, and the release layer tube or coating remains on the surface of the mandrel. As the assembly is heated, the first tube softens and becomes heat flowable. The second tube then shrinks forcing the heat flowable material into the gaps between the turns of the helical coil 5 at least partially enveloping it. Preferably the heat flowable material substantially completely envelopes the helical coil. The flowable material flows between the mandrel and the coil. A circular cross-section helix wire is preferred since there is a smaller area of wire adjacent to the mandrel than if say a square cross section wire of the same cross-sectional area were used. In positions along the length of the assembly where the coil is not present, greater shrinkage takes place and this allows formation of the preferred tapered tip 20, see FIG. 1a. The tip may be shaped and dimensioned to accept a hollow needle so that, in use, a needle of corresponding size can be fitted to the catheter tip prior to use. This step of shaping and dimensioning the tip may be carried out by introducing a suitable, smaller size mandrel into the tip portion and further shrinking the first tube onto this mandrel before removing the second tube. The smaller size tip mandrel is then removed and the tip is then able to hold a hollow needle in frictional engagement when inserted into the tip. In making the tapered tip, the mandrel may be removed and a slightly smaller one introduced. This may have a release surface. The tip region may then be heated, e.g. in an annular heater so that heating is confined to the tip. The heat shrinkable tube 20 may be slightly longer than the tube 4. On heating, a taper is formed and the second tube can be removed starting from the tip 201.

The precise temperature to which the assembly should be heated depends on the nature of the polymers. The first tube is generally flowable at a temperature in the range of 100 to 300° C. The second tube is generally selected to be heat shrinkable at a temperature about 50 to 100° C. higher than the temperature at which the plastics material of the first tube becomes flowable. Typically therefore the second tube heat shrinks at a temperature in the range 150 to 350° C. Temperatures higher than 350° C. are generally not preferred.

The mandrel 100 if present can be removed and the catheter processed further for example in conventional manner by attaching, e.g. by welding, adhesively bonding or insert moulding the catheter to the hub 30.

After the heat shrink step is completed, the second tube may be removed, leaving the coil substantially embedded in the wall of the first tube. This results in a reinforced catheter having a smaller overall diameter. The second tube is conveniently removed, e.g. by slitting and peeling it away from the first tube, while the first tube is still supported on the mandrel or on a further mandrel. The mandrel may then be removed. To facilitate removal of the second tube, it is preferably longer than the first tube or positioned relatively to the first tube so that it extends beyond the end of the first tube as shown in FIG. 1a. The overlapping portion 201 can then more easily be slit and peeled away without damage to the first tube. A reinforced catheter as produced by this method is shown in FIG. 5.

Catheters manufactured in accordance with this invention are particularly useful for introducing sensors, e.g. optical sensors, into a patient's blood vessel for monitoring parameters such as blood oxygen, $CO_2$ and pH. The reinforced catheter protects the delicate sensor while retaining the necessary flexibility for passing the catheter into a blood vessel. Examples of typical optical sensors are those manufactured by Diametrics Medical Limited of Short Street, High Wycombe, England under the trade mark 'Paratrend', and described in U.S. Pat. Nos. 4,889,407 and 5,262,037, the disclosure of which is specifically incorporated herein by reference.

As explained above, in some embodiments of the invention the outer layer or second tube is stripped away once the heat flowing has occurred. To aid this it may be desirable to provide a release agent between the two tubes or to select as the material of one of the tubes a polymer which has good release properties. For example, the selection of PTFE or FEP as the material of the second tube provides such release properties. Stripping away of the outer layer provides a more flexible and thinner catheter which may therefore be preferred. A preferred technique is to provide a stainless steel mandrel covered with a thin PTFE tube and to support the helical spring on such a mandrel, while forming the reinforced catheter comprising a first, heat-flowable tube, and a second heat-shrinkable tube. After the heat-shrinking step, the mandrel and thin PTFE tube is removed and replaced with a stainless steel wire of larger diameter than the mandrel. Using this wire as a support, the heat-shrinkable second tube is slit and peeled away to leave the first tube encapsulating the helical spring.

Figure 5:
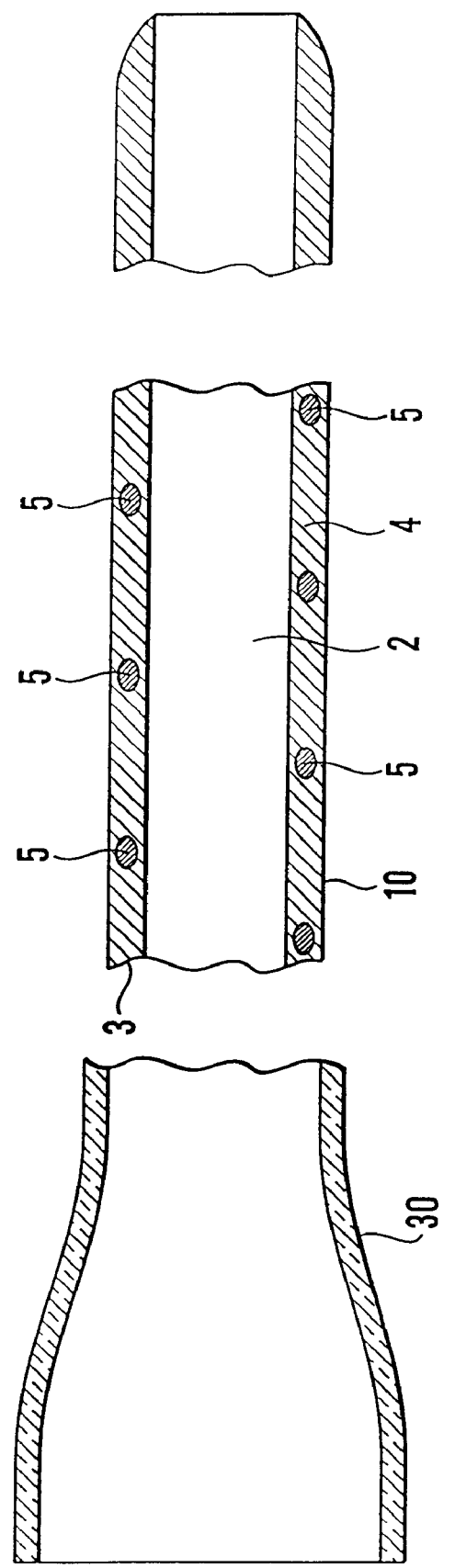
FIG. 5 is a scrap section of a second embodiment of a catheter of the invention.

FIG. 5a illustrates the situation after the heat-shrinking step and after removal of the mandrel, but before removal of the thin PTFE sheathing tube 101 from within the catheter. The tube 101 is preferably arranged to be longer than the tube 4 so that portions 102 project from both ends. Tube 101 is readily removed to provide the finished catheter shown in FIG. 5 by grasping the projecting ends 102 and pulling them outwardly in opposite directions. This is sufficient to cleanly break the bond between the tube 101 and the inner surface of the tube 4 and the whole tube 101 can then be removed. Of course, the tube 101 can be removed before or after removing the second, outer tube 20.

For ease of manufacture and subsequent removal of the second tube and the sheathing release tube, the sheathing tube is preferably longer tan the first and second tubes and the second tube is longer than the first.

In some embodiments of the invention a further tube is provided between the helical coil and the mandrel and is chosen to bond with the further tube. This helps to ensure that the coil is encapsulated by plastics materials. It may be preferable for the further tube and the first tube to be of the same or similar polymer composition. In this embodiment, the first tube is formed from FEP and the second tube from PTFE or a higher melting grade of FEP. The catheter is manufactured as follows. A mandrel carrying a tube of FEP is inserted into a helical coil, which is introduced into a second tube of PTFE or higher melting FEP. The resulting assembly is heated and the second tube shrinks onto the helical coil, causing some FEP to flow between the coils and to bond to the second tube. In this embodiment, it is not possible to remove the outer tube but the two tubes bond together strongly to encapsulate the coil. The mandrel is then removed. A tapered tip can be produced by selecting an outer tube which is longer than the first tube, and a helical spring which is shorter than both. The end can then be trimmed as a final step.

In the case of preferred materials, PTFE and FEP tubing available from Zeus, Orangebury, S.C., USA, the PTFE shrinks at a temperature in the range 335–343° C. (635–650° F.) and the FEP flows at 260–277° C. (500–530° F.).

As explained above, the reinforced catheters of this invention may be introduced into a blood vessel using the hollow needle and wire technique, known as the Seldinger technique. In order to reduce the trauma arising from the direct introduction of the reinforced catheter of the invention into a blood vessel, a system transition from a smaller to a larger system may be adopted, such as the system described in U.S. Pat. No. 4,650,472, the disclosure of which is specifically incorporated herein by reference.

I claim:

1. A method of making a kink-resistant catheter; the method comprising forming an assembly by:
   (a) supporting a helical metallic coil having a plurality of turns on a mandrel;
      (i) the mandrel supporting a sheathing tube comprising polytetrafluoroethylene (PTFE) or fluorinated ethylene propylene copolymer (FEP);
   (b) introducing the helical coil while supported on the mandrel into a first tube;
      (i) the first tube being formed from a material which is flowable at a first temperature; and
      (ii) the first tube being received within a second tube to form an assembly;
         (A) the second tube being heat shrinkable at a second temperature which is equal to or greater than the first temperature;
   (c) heating the assembly to a temperature equal to or greater than the second temperature to cause shrinkage of the second tube;
      (i) the shrinkage of the second tube causing material of the first tube to flow between turns of the helical coil and substantially encapsulate the helical coil;
   (d) removing the mandrel from at least the first tube and the helical coil while leaving the sheathing tube within the helical coil; and
   (e) longitudinally tensioning the sheathing tube to remove the sheathing tube from at least the first tube and the helical coil.

2. A method as claimed in claim 1 wherein:
   (a) the sheathing tube is longer than the helical coil, the first tube, and the second tube; and
   (b) the sheathing tube extends beyond one or both ends of the helical coil, the first tube, and the second tube; and
   (c) the step of removing the sheathing tube includes pulling on one or both ends of the sheathing tube.

3. A method as claimed in claim 2 wherein:
   (a) the helical coil is shorter than the first tube and is positioned on the mandrel so that the first tube extends beyond one or both ends of the helical coil; and
   (b) the step of heating the assembly causes an inwardly tapered tip to be formed at one or both ends of the helical coil.

4. A method as claimed in claim 1 further including:
   (a) after the step of heating, removing the second tube from the first tube and the helical coil.

5. A method as claimed in claim 4 wherein:
   (a) the step of removing the second tube includes slitting the second tube.

6. A method as claimed in claim 1 wherein:
   (a) the first tube is heat flowable at a first temperature in the range of 100 to 300° C.; and
   (b) the second tube is heat shrinkable at a second temperature greater than the first temperature and in the range of 150 to 350° C.

* * * * *

UNITED STATES PATENT AND TRADEMARK OFFICE
CERTIFICATE OF CORRECTION

PATENT NO. : 6,702,972 B1
DATED : March 9, 2004
INVENTOR(S) : David Reed Markle

It is certified that error appears in the above-identified patent and that said Letters Patent is hereby corrected as shown below:

<u>Title page,</u>
Item [63], Related U.S. Application Data, second line, after "which is a" delete "continuation" and insert -- continuation-in-part --.

Signed and Sealed this

Twenty-fourth Day of August, 2004

JON W. DUDAS
*Director of the United States Patent and Trademark Office*